(12) United States Patent  
Alexander, Jr. et al.

(10) Patent No.: US 6,187,022 B1
(45) Date of Patent: Feb. 13, 2001

(54) APPARATUS AND METHOD FOR IMPROVED AORTIC INCISION

(75) Inventors: John C. Alexander, Jr., Ridgewood, NJ (US); Carl A. Swindle, Dana Point, CA (US)

(73) Assignee: Edwards Lifesciences Corporation, Irvine, CA (US)

( * ) Notice: Under 35 U.S.C. 154(b), the term of this patent shall be extended for 0 days.

(21) Appl. No.: 09/511,666

(22) Filed: Feb. 23, 2000

Related U.S. Application Data

(63) Continuation of application No. 09/273,030, filed on Mar. 19, 1999, now Pat. No. 6,083,238, which is a continuation-in-part of application No. 08/935,816, filed on Sep. 23, 1997, now Pat. No. 5,893,865.

(51) Int. Cl.$^7$ ..................................................... A61B 17/00
(52) U.S. Cl. ........................ 606/185; 606/167; 606/153; 30/366
(58) Field of Search .............................. 606/1, 166, 167, 606/184, 185, 153; 604/158, 164, 165, 264; 30/366

(56) References Cited

U.S. PATENT DOCUMENTS

| | | |
|---|---|---|
| D. 291,595 | 8/1987 | Armstrong . |
| D. 332,492 | 1/1993 | Rosenberg et al. . |
| 2,649,860 | 8/1953 | Royer . |
| 4,018,228 | 4/1977 | Goosen . |
| 4,349,202 | 9/1982 | Scott . |
| 4,365,957 | 12/1982 | Das . |
| 4,468,038 | 8/1984 | Saunders . |
| 4,570,941 | 2/1986 | Saunders . |
| 4,832,045 | 5/1989 | Goldberger . |
| 4,862,591 | 9/1989 | Barringer . |
| 4,873,976 | 10/1989 | Schreiber . |
| 4,891,887 | 1/1990 | Witte . |
| 5,066,288 | 11/1991 | Deniegar et al. . |
| 5,135,525 | 8/1992 | Biscoping et al. . |
| 5,196,024 | 3/1993 | Barath . |
| 5,275,583 | 1/1994 | Crainich . |
| 5,447,516 | 9/1995 | Gardner . |
| 5,452,733 | 9/1995 | Sterman et al. . |
| 5,507,765 | 4/1996 | Mott . |
| 5,554,137 | 9/1996 | Young et al. . |
| 5,554,167 | 9/1996 | Young . |
| 5,591,186 | 1/1997 | Wurster et al. . |
| 5,591,192 | 1/1997 | Privitera et al. . |
| 5,609,604 | 3/1997 | Schwemberger et al. . |
| 5,620,456 | 4/1997 | Sauer et al. . |
| 5,624,459 | 4/1997 | Kortenbach et al. . |
| 5,735,290 | 4/1998 | Sterman et al. . |
| 5,797,944 | 8/1998 | Nobels et al. . |

Primary Examiner—Michael Buiz
Assistant Examiner—William Lewis
(74) Attorney, Agent, or Firm—Workman, Nydegger & Seeley

(57) ABSTRACT

A surgical knife which provides improved multi-sided incisions and is preferably allows for a substantially cruciate, or cross-shaped incision. The surgical knife includes a handle and a multi-bladed portion located at one end of the handle. The handle is sized and configured to maximize grip and surgical manipulation thereof. The multi-bladed portion is formed from a primary blade and a secondary blade. The primary blade is configured with two exemplary primary blade members. The primary blade members are formed with sharpened edges which combined to form a sharpened distal point of the primary blade. The secondary blade is formed with sharpened edges and cooperates with the primary blade. The coupling of the primary blade and the secondary blade is such that the distal end of the secondary blade is located at a distance from the sharpened distal point of the primary blade. The combination of the primary and secondary blades form a multi-bladed portion which creates an improved, more precise and easier to control incision in a biological tissue. The surgical knife is especially useful, for example, in improved aortotomies.

13 Claims, 10 Drawing Sheets

APPARATUS AND METHOD FOR IMPROVED AORTIC INCISION

RELATED APPLICATION

This application is a continuation of Ser. No. 09/273,030, filed Mar. 19, 1999 now U.S. Pat. No. 6,083,238 which is a continuation-in-part of a United States patent application entitled "Apparatus and Method for Improved Aortic Incision," filed on Sep. 23, 1997, Ser. No. 08/935,816, now U.S. Pat. No. 5,893,865 which is incorporated herein by reference.

BACKGROUND OF THE INVENTION

1. The Field of the Invention

The present invention is directed generally to methods and apparatus for effectuating surgical incisions. More specifically, the present invention is related to methods and apparatus for effectuating precise and uniform incisions, including aortic incisions.

2. The Relevant Technology

Coronary artery bypass surgery is commonly required when coronary arteries narrowed by cholesterol-rich fatty deposits or plaques are unable to supply the heart muscle with a sufficient amount of blood, and as a result, the heart becomes starved for oxygen. Left untreated, coronary artery disease ultimately leads to acute myocardial infarction, commonly referred to as a heart attack. In coronary artery bypass surgery, a surgeon grafts a section of a healthy vessel, such as a portion of a saphenous vein, to bypass a stenotic or partially blocked portion of a coronary artery in order to ameliorate the oxygen access to the heart muscle.

Various techniques have been used to create the opening in the aorta, known as an aortotomy, to which the graft is sutured. Most aortotomies used for bypass grafts are created using a surgical scalpel in concert with an aortic punch. The surgical scalpel is used to make a linear incision in the aorta Then, a portion of the aortic punch known as the "anvil" is passed through the incision. The punch is then engaged creating an aortotomy.

Conventionally, in order for the anvil of the punch to pass through the linear incision, either the incision needs to be longer than the diameter of the anvil or the hole created by the incision needs to be stretched. When the incision is made longer than the punch diameter, lateral nicks in the circumference of the aortotomy are created. These lateral nicks necessitate either repunching the aorta to enlarge the aortotomy or special suturing to avert bleeding at the lateral incision sites. Alternatively, when the initial hole created by the incision is stretched, often by utilizing a dilator prior to inserting the punch, an irregular and unpredictable tearing of the aorta often occurs.

The brittle and fragile nature of the aorta in the average coronary artery bypass graft patient necessitates great care in dealing with the aortic wall. The problems associated with conventional aortotomies can cause major problems with bleeding, compromise of the anastomosis, or aortic dissection.

Similar problems exist with incisions made in other vessels and even other body organs. Therefore, it will be advantageous to provide an improved method and apparatus for performing improved incisions.

SUMMARY AND OBJECTS OF THE INVENTION

It is an object of the present invention to provide improved methods and apparatus for achieving precise and uniform surgical incisions.

It is another object of the present invention to provide improved methods and apparatus for providing aortotomies for coronary artery bypass grafts.

It is still another object of the present invention to provide improved methods and apparatus for providing aortotomies which do not require stretching or repunching.

These and other objects and features of the present invention will become more fully apparent from the following description and appended claims, or may be learned by the practice of the invention as set forth hereinafter.

The present invention is directed to a surgical knife which provides the unique feature of multi-sided incisions, for example, within an aorta for effectuating improved aortotomies. The surgical knife preferably includes a multi-bladed portion connected to a handle portion. The handle is sized and configured to maximize grip and surgical manipulation thereof. In one configuration, the multi-bladed portion extends to a sharpened distal point with a plurality of blade members radiating outwardly and proximally from the sharpened point. Each blade member is formed with a sharpened edge. A preferred surgical knife provides a substantially cruciate, or cross-shaped, incision with four sharpened blade members.

In a preferred embodiment of the present invention, the multi-bladed portion is formed from a primary blade and a secondary blade. The primary blade has a sharpened distal point and the secondary blade has a distal end. The primary and secondary blades are joined such that the distal end of the secondary blade is at a location spaced proximally from the sharpened distal point of the primary blade. The primary blade may be configured with two or more primary blade members, each formed with a sharpened edge. The primary blade members combine to form a sharpened distal point. The secondary blade may be formed from two or more secondary blade members which combine to form a distal end of the secondary blade.

The multi-bladed portion of the surgical knife may comprise three, four, five, six, or more blade members. It is currently preferred that the blade members form equal angles in radiation outwardly and proximally from the sharpened distal point such that, in the preferred embodiment, the surgical knife provides a substantially cruciate, or cross-shaped, incision with limited force applied by a user.

In a preferred method of the present invention, an appropriate site and size for an incision is determined. An appropriately sized surgical knife having a primary and a secondary blade of the present invention is obtained and then inserted perpendicularly into the predetermined site. In another preferred method of the present invention, an appropriately sized surgical or aortic knife is obtained and stabbed into a portion of an aorta or other vessel, or other body organ. An anvil of an aortic punch is then inserted into the incision, for example, in the aorta, a step that may be performed without the stretching necessitated by the conventional single linear incision. The punch is then centered and fired. The resulting aortotomy lacks the lateral nicks and aortic dissection associated with the prior art.

BRIEF DESCRIPTION OF THE DRAWINGS

In order to more fully understand the manner in which the above-recited and other advantages and objects of the invention are obtained, a more particular description of the invention will be rendered by reference to a specific embodiment thereof which is illustrated in the appended drawings. Understanding that these drawings depict only a typical embodiment of the invention and are not therefore to be considered to be limiting of its scope, the invention in its presently understood best mode for making and using the same will be described and explained with additional specificity and detail through the use of the accompanying drawings in which.

DETAILED DESCRIPTION OF THE PREFERRED EMBODIMENTS

In coronary artery bypass surgery, a surgeon grafts a section of a healthy vessel, such as a portion of the saphenous vein or other suitable material, to bypass a partially blocked portion of a coronary artery in order to improve the oxygen delivery to the heart muscle. Various techniques have been used to create the opening in the aorta, known as an aortotomy, to which the graft is sutured. Most aortotomies used for bypass grafts are created using a surgical scalpel in concert with an aortic punch. However, this conventional technique is imprecise at best, and the resulting graft is often compromised.

Figure 1:
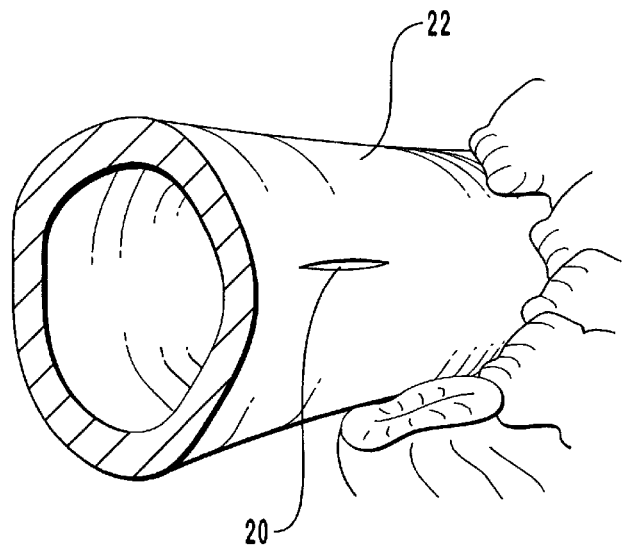
FIG. 1 is an illustration of an incision in an aorta provided by a conventional scalpel.
Figure 2:
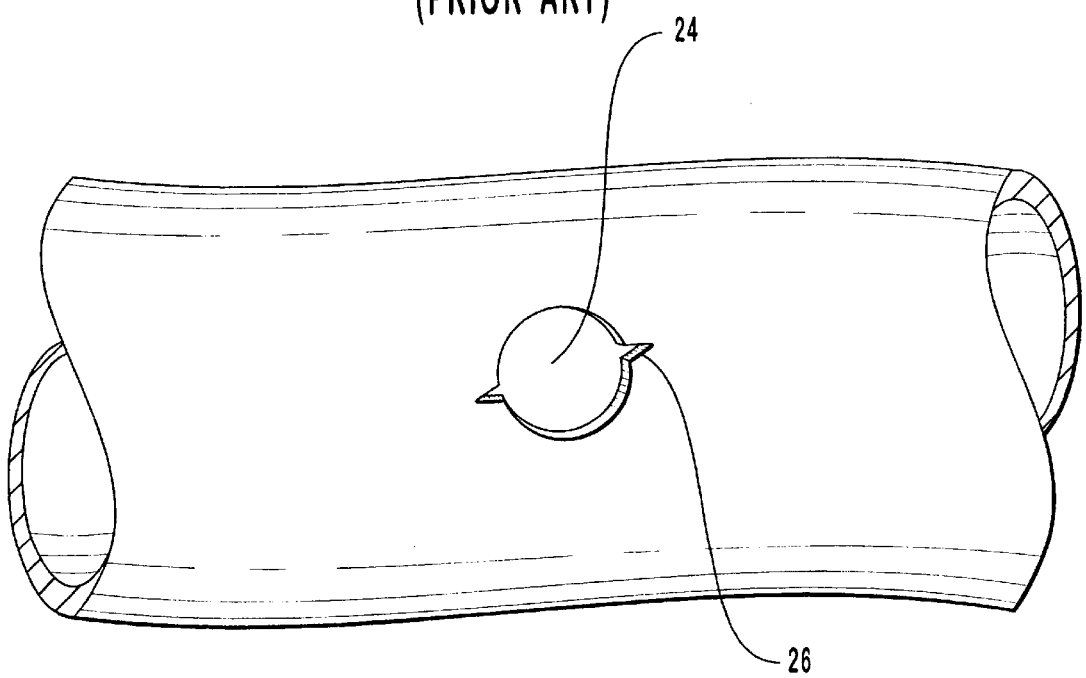
FIG. 2 is an illustration of an aortotomy resulting from an aortic punch used in concert with the incision in FIG. 1.

FIG. 1, for example, illustrates a conventional linear incision 20 along an aorta 22 utilizing a conventional scalpel. In performing such an incision, the surgeon makes an educated guess as to the length of the incision. FIG. 2 illustrates the resulting aortotomy 24 wherein lateral nicks 26 are clearly visible. These nicks necessitate special suturing to prevent blood leakage, and add points of weakness at the site of the vessel graft.

Alternatively, a surgeon may make an incision that is smaller than the diameter of the punch such that lateral nicks might be avoided. However, such an incision necessitates stretching of the tissue for insertion of the aortic punch anvil. In turn, the stretching of the tissue can decrease the patency of the resulting graft or can cause aortic dissection wherein the layers of the aortic wall separate from one another.

Figure 3:
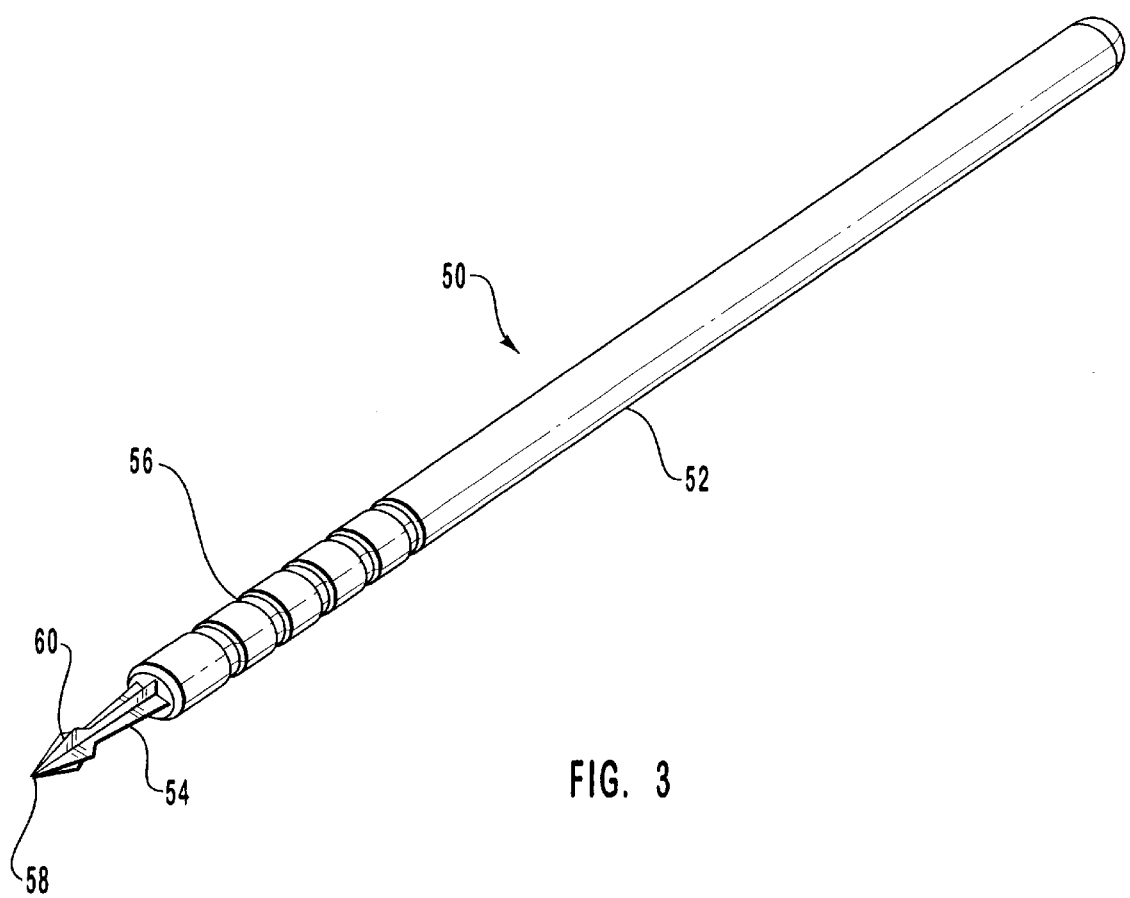
FIG. 3 is a partial perspective view of one embodiment of a surgical or an aortic knife in accordance with the present invention.

In contrast, the present invention is directed to a precisely-sized, multi-bladed knife for effectuating an improved incision or biological tissue entry. FIG. 3, for example, illustrates one embodiment of a surgical or an aortic knife, represented generally by numeral 50. Aortic knife 50 of the present invention preferably includes a multi-bladed portion 54 attached to a handle 52.

The handle 52 preferably comprises a rigid material such as steel, plastic, or wood. As should be appreciated by reference to FIG. 3, the handle includes a grip portion 56 to improve a surgeon's grasp and prevent slipping of the knife. The handle is preferably sized to maximize surgical manipulation thereof.

Figure 4:
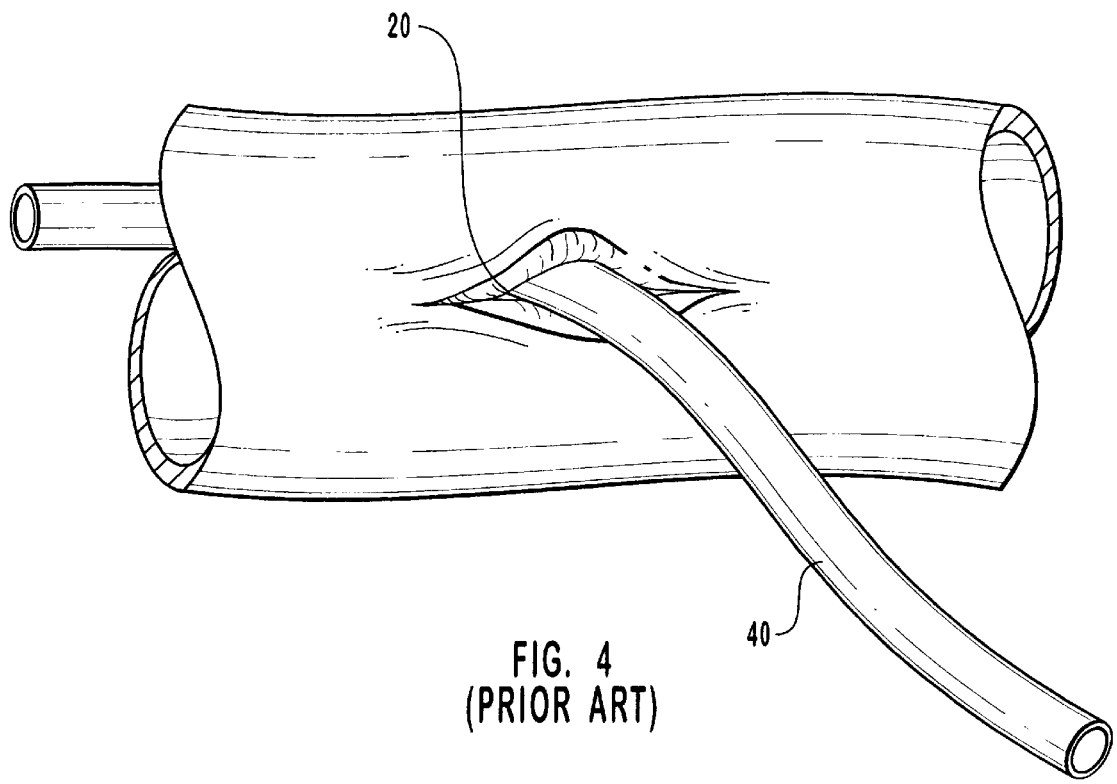
FIG. 4 is an illustration of cannulation through an incision in a vessel provided by a conventional scalpel.
Figure 5:
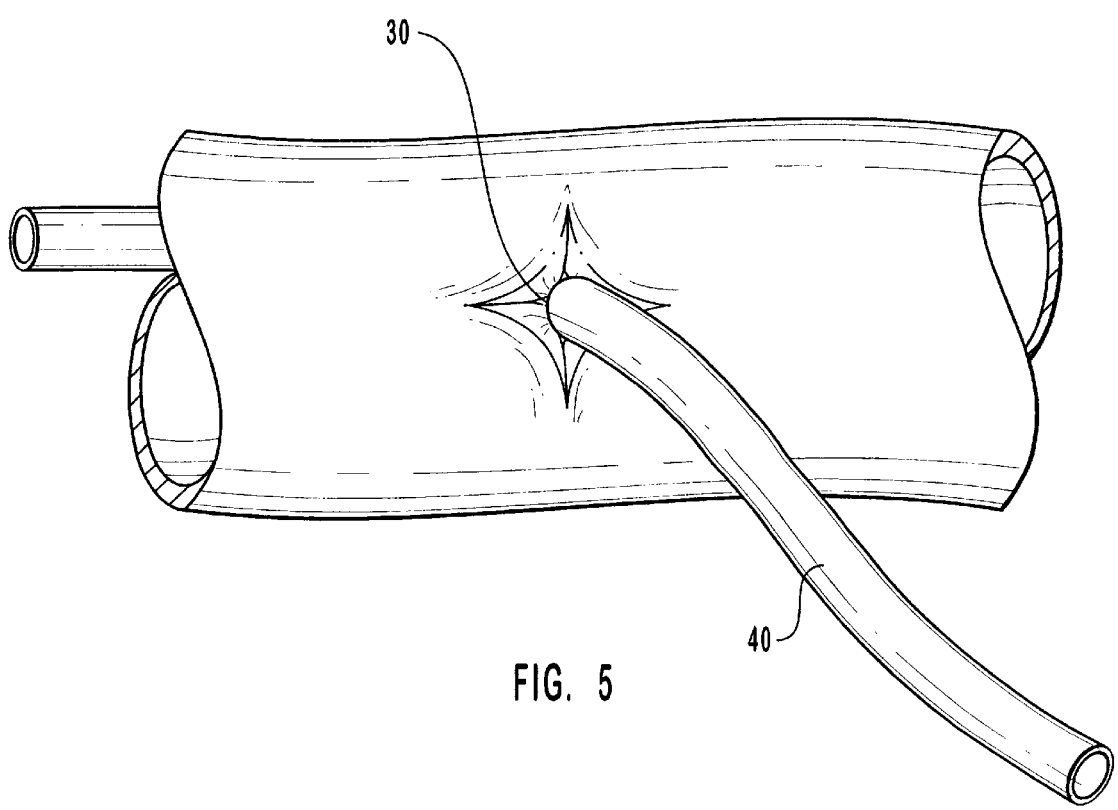
FIG. 5 is an illustration of cannulation through an incision in a vessel provided by an aortic knife in accordance with the present invention.

The multi-bladed portion 54 of aortic knife 50 provides multiple cutting surfaces, which results in an incision which displaces the tissue in multiple directions, and facilitates insertion of medical devices such as cannulae or aortic punches. When a surgical instrument is introduced into the multi-sided incision, the tissue displaces circumferentially around the instrument, whereas the conventional incision results in linear tissue displacement which requires the tissue to stretch around the instrument. FIG. 4, for example, illustrates the linear tissue displacement which occurs upon the insertion of a cannula 40 through a conventional incision 20. In contrast, FIG. 5 illustrates the inward and circumferential tissue displacement around the cannula 40 when the cannula is introduced into a multi-sided incision 30 in accordance with the present invention.

In one embodiment of the present invention, aortic knife 50 comprises multi-bladed portion 54 formed from four blade members, each blade member being separated from each other blade member by 90 degrees. The resulting shape of the incision is substantially cruciate or cross-shaped, and thus substantially resembles a "+" configuration. As illustrated in FIG. 3, multi-bladed portion 54 of aortic knife 50 preferably extends distally to a sharpened point 58, which facilitates perpendicular insertion of aortic knife 50 into the aorta, other vessel, or any other biological tissue. Each blade member of multi-bladed portion 54 has a sharpened edge 60 which radiates outwardly and proximally from the sharpened distal point 58.

Once sharpened distal point 58 is perpendicularly stabbed into a vessel, sharpened edges 60 slide into the vessel and provide the improved incision. The resulting incisions are situated circumferentially around the central stabbed portion, which effectuates inward displacement of the tissue in four directions upon insertion of a surgical instrument. The preferred four-sided, or cruciate, incision of the present invention facilitates insertion of a punch anvil and thus reduces trauma to the aortic wall.

Figure 6:
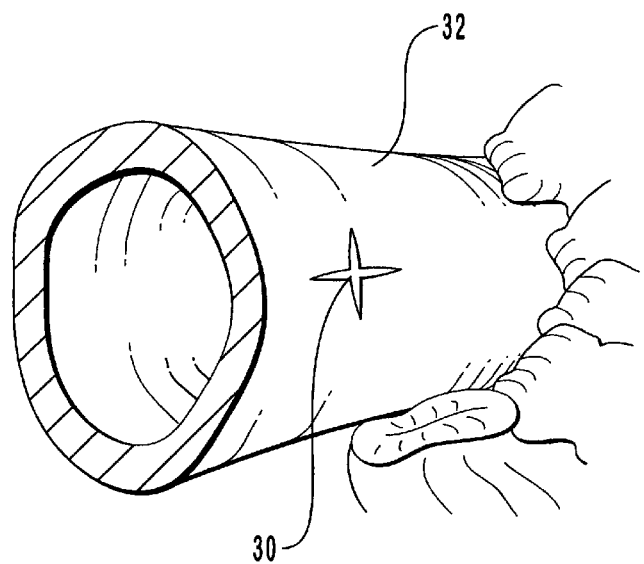
FIG. 6 is an illustration of an incision in an aorta provided by an aortic knife in accordance with the present invention.
Figure 7:
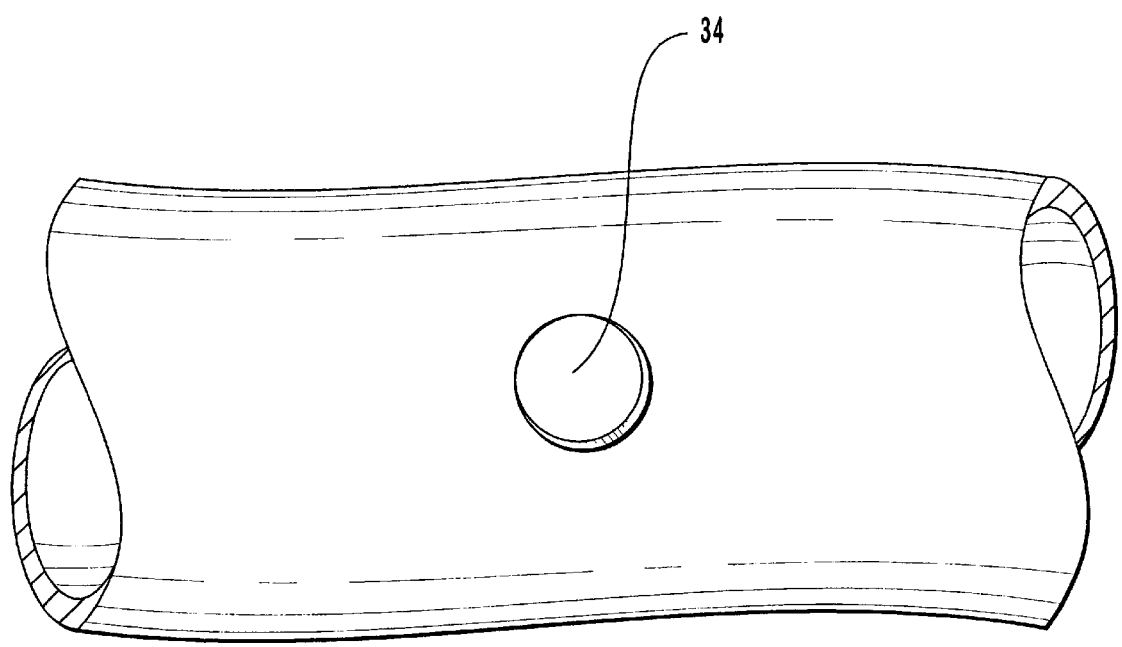
FIG. 7 is an illustration of an aortotomy resulting from an aortic punch used in concert with an incision such as provided in FIG. 6.
Figure 8:
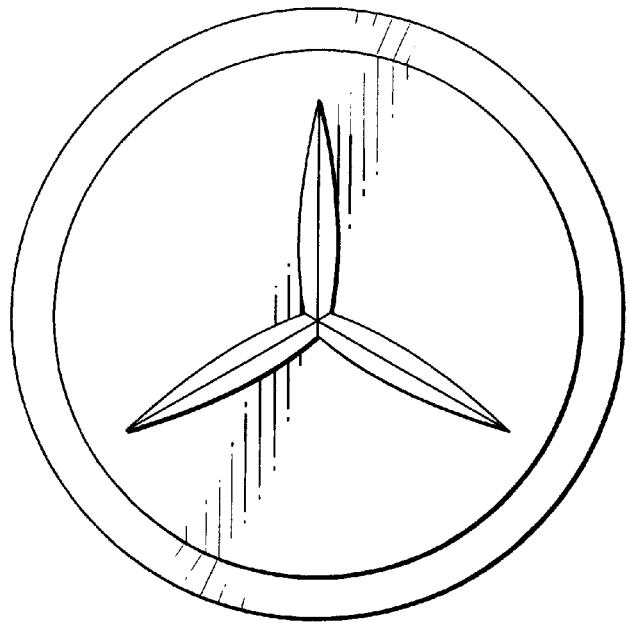
FIG. 8 is an end view of an alternate embodiment of the multi-bladed portion of a surgical knife in accordance with the present invention.
Figure 9:
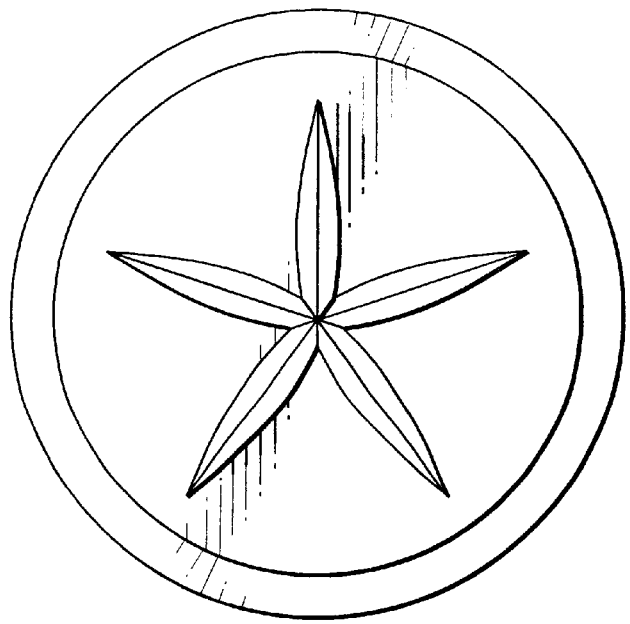
FIG. 9 is an end view of yet another alternate embodiment of the multi-bladed portion of a surgical knife in accordance with the present invention.

FIG. 6, for example, illustrates a stabbed cruciate incision 30 through an aorta 32 made by aortic knife 50 of FIG. 3. FIG. 7 illustrates the resulting aortotomy 34 after the utilization of an aortic punch preferably sized to correspond to the size of aortic knife 50. The aortotomy 34 is substantially uniform and circular in shape and clearly lacks the lateral nicks of the prior at Alternatively, aortic knife 50 in accordance with the present invention may comprise any number of blade members to form multi-bladed portion 54, and preferably comprises at least three. It is further preferred that the arrangement of the blade members around sharpened distal point 58 of multi-bladed portion 54 is such that the angles separating the blade members are equal. For example, in an embodiment comprising three blade members, each blade member is separated from each other blade member by about 120 degrees. FIG. 8 illustrates an end view of such a three-blade member configuration. In an alternate embodiment illustrated in FIG. 9, multi-bladed portion 54 is configured into a stellate, or star-shape, configuration with five blade members radiating outwardly at about 72 degree angles.

It should be appreciated that the blade members can alternatively be separated from each other by angles of differing degrees. Equal angles are preferred, but the present invention is not limited to such a configuration.

Figure 10:
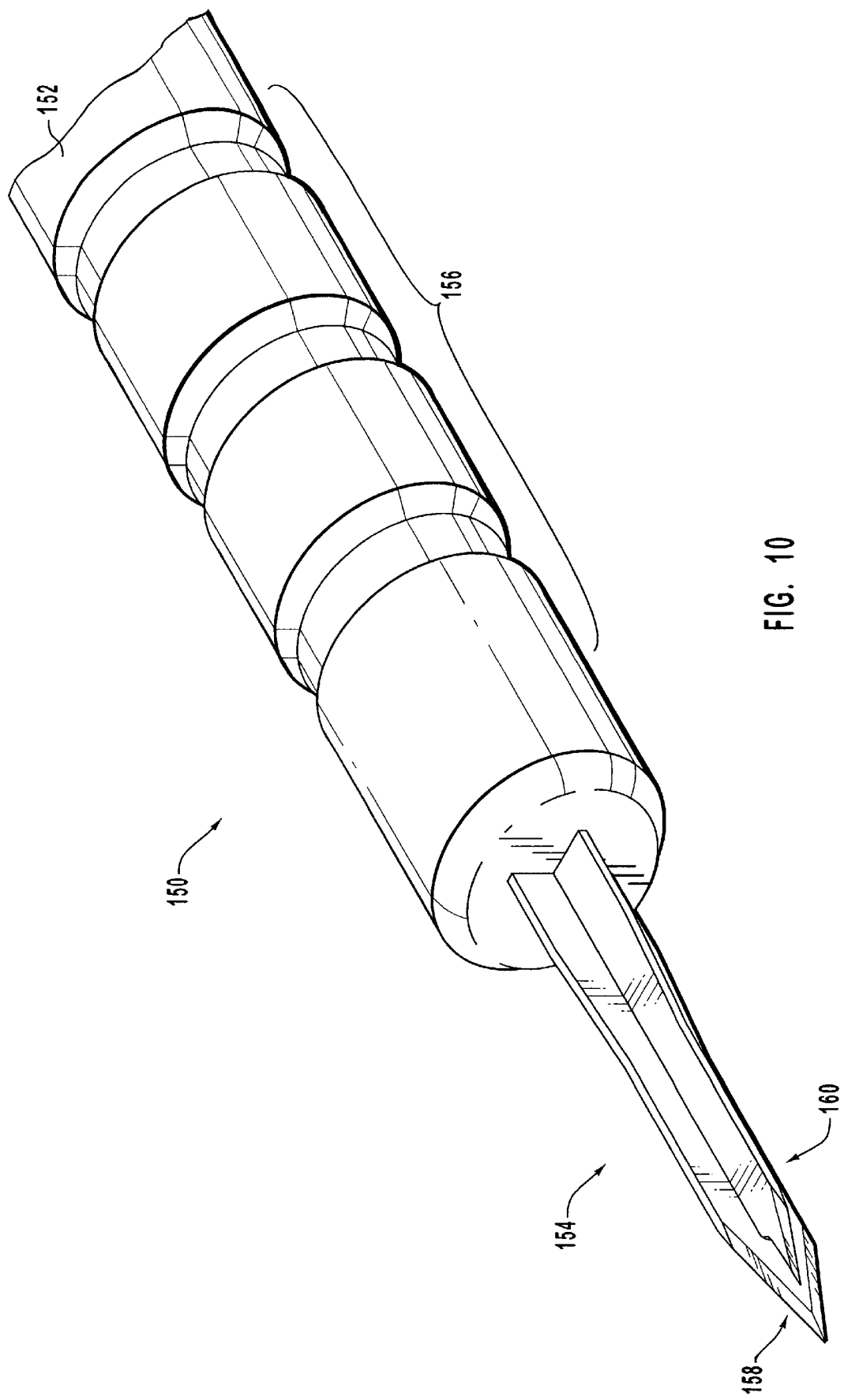
FIG. 10 is a partial perspective view of yet another alternate embodiment of a surgical knife in accordance with the present invention.

FIG. 10 illustrates different and preferred embodiment of a surgical knife 150 of the present invention that provides a unique and improved incision into a biological tissue and that significantly improves a surgeon's ability to create a precise incision, for example, a proximal anastomotic site.

Surgical knife 150 includes a multi-bladed portion 154 attached to a handle 152. As with handle 52, handle 152 includes a grip portion 156 which improves a surgeon's grasp and prevents slipping of the knife. Multi-bladed portion 154 is however different from that of multi-bladed portion 54.

Figure 11:
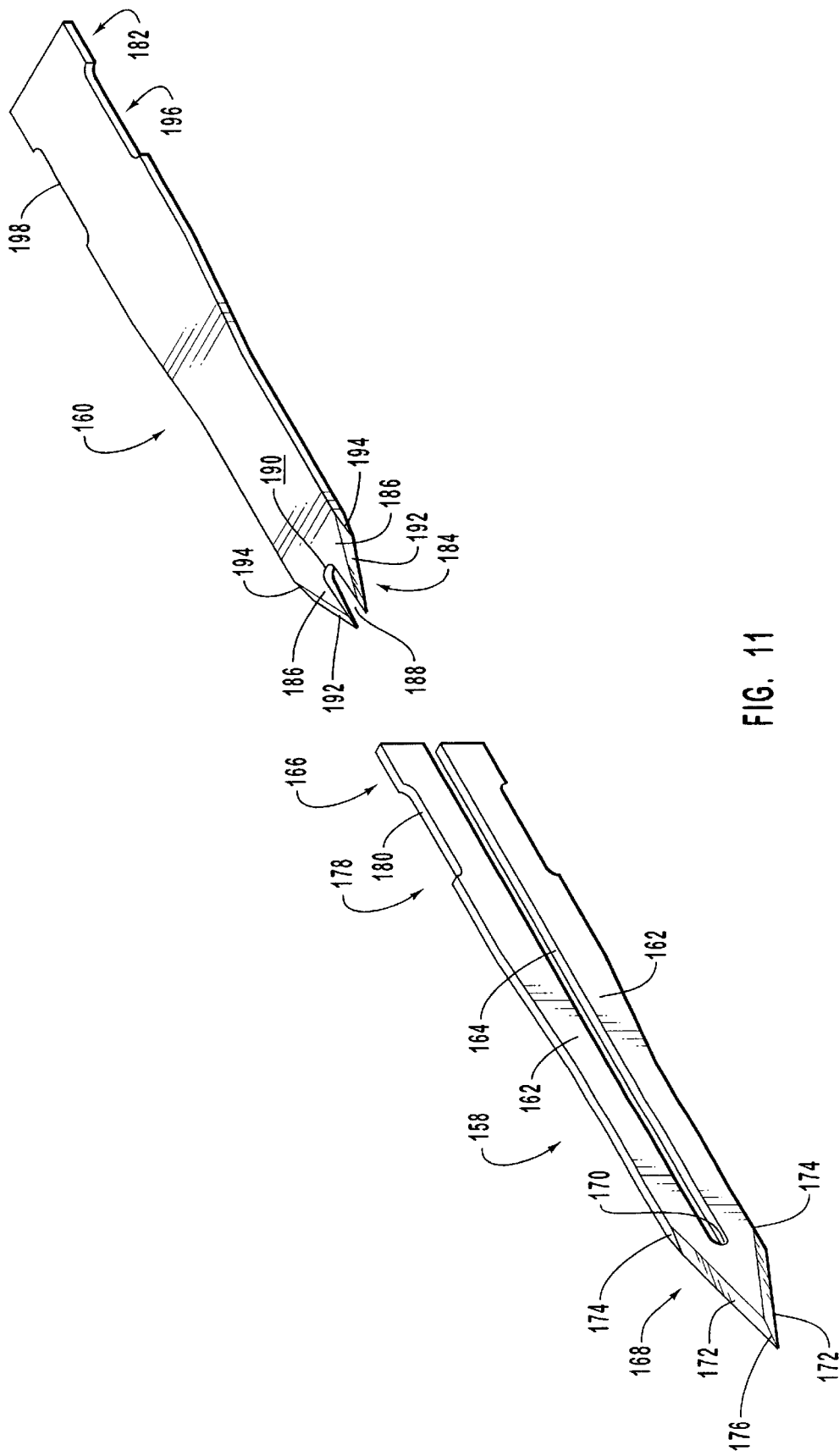
FIG. 11 is an exploded perspective view of the multi-bladed portion of the alternate embodiment of FIG. 10.

In the specific configuration, shown in FIG. 10, multi-bladed portion 154 is formed from a primary blade 158 and a secondary blade 160 and it has a longitudinal axis 159. Referring now to FIG. 11, by way of example and not limitation primary blade 158 has a generally ensate or sword-shaped form and is divided into two mirror-image blade members 162 by a slot 164. Slot 164 extends longitudinally from a proximal end 166 of primary blade 158 towards a distal end 168, terminating in a bifurcation point 170 in close proximity to a sharpened distal point 176. Each blade member 162 is provided with a sharpened edge 172 that begins at an apex 174 on the peripheral edge of each blade member 162 and converges to form sharpened distal point 176. Located at proximal end 166 of each blade member 162 is a securing portion 178 which is formed with a recess 180 to aid in fixably attaching primary blade 158 within handle 152.

Secondary blade 160 has a generally ensate or sword-shaped form having a proximal end 182 and a distal end 184. Distal end 184 is formed with two mirror-image blade members 186 separated by a slot 188. Slot 188 extends longitudinally from distal end 184 of secondary blade 160 towards proximal end 182, terminating in a bifurcation point 190. Each blade member 186 is formed with a sharpened edge 192 that begins at an apex 194 on the peripheral edge of each blade member 186 and ends at distal end 184 thereof. Slot 188 is formed to cooperate with slot 164 such that primary blade 158 and secondary blade 160 may be securely coupled together and fixably attached to handle 152. Located at proximal end 182 of secondary blade 160 is a securing portion 196 which is formed with a recess 198 to aid in fixably attaching secondary blade 160 within handle 152, as shown in FIG. 10. Of course, any other conventional and appropriate means of attachment of the multi-bladed portion 154 to handle 152 are within the scope of the present invention.

In the embodiment of FIG. 11, to form multi-bladed portion 154, secondary blade 160 is positioned within slot 164 of primary blade 158. Distal end 184 of secondary blade 160 is moved towards distal end 168 of primary blade 158 until slot 188 of secondary blade 160 is coupled at distal end 168. As slot 188 of secondary blade 160 is coupled at distal end 168, bifurcation point 170 and bifurcation point 190 substantially coincide with each other. By coupling primary blade 158 and secondary blade 160 in such a manner, apex 194 of blade members 186 and apex 174 of blade members 162 may be coincided upon a plane perpendicular to the longitudinal axis of aortic knife 150. As apexes 174 and 194 lie upon the same plane, distal end 184 of secondary blade 160 is at a location spaced from sharpened distal point 176 of primary blade 158 in a proximal direction along the longitudinal axis 159. The spacing between distal end 184 of secondary blade 160 and sharpened distal point 176 is achieved through the combination of both the location of the bifurcation points 170 and 190 and the angle at which each sharpened edge 172 and 192 is formed relative to the longitudinal axis of aortic knife 150. One way to achieve the coincidence of apexes 174 and 194 upon a plane is to make the angle between the longitudinal axis and sharpened edge 172 of primary blade 158 smaller than the angle created between the longitudinal axis and sharpened edges 192 of secondary blade 160. While it is not required, such coincidence of apexes is preferred. Further, in other configurations of surgical knife 150 the angle, relative to the longitudinal axis of surgical knife 150, at which sharpened edges 172 and 192 are formed may vary so long as the functionality of surgical knife 150 is maintained.

In general, surgical knife 150 may have various other configurations so long as distal end 184 of secondary blade 160 is at a location longitudinally spaced from sharpened distal point 176 of primary blade 158. The distance of spacing between the distal end 184 and the sharpened distal point 176 may vary dependent on the size of the surgical knife, the size of the intended incision and the location of the incision. Preferably, the distal end 184 of the secondary blade is close to the dital point of the primary blade, and more preferably is not spaced in a proximal direction substantially past the longitudinal position of apex 174 of the primary blade.

Figure 12:
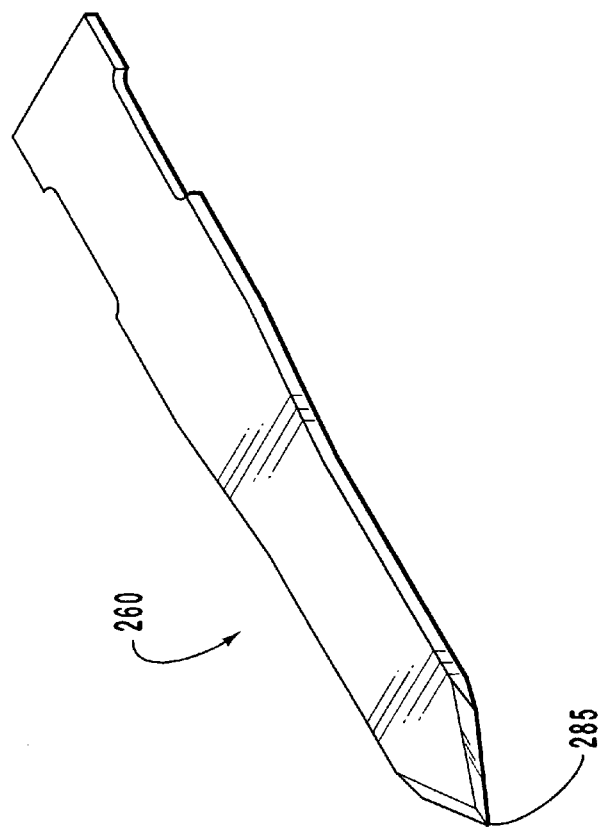
FIG. 12 is an exploded perspective view of another configuration of the alternate embodiment of FIG. 10.
Figure 12:
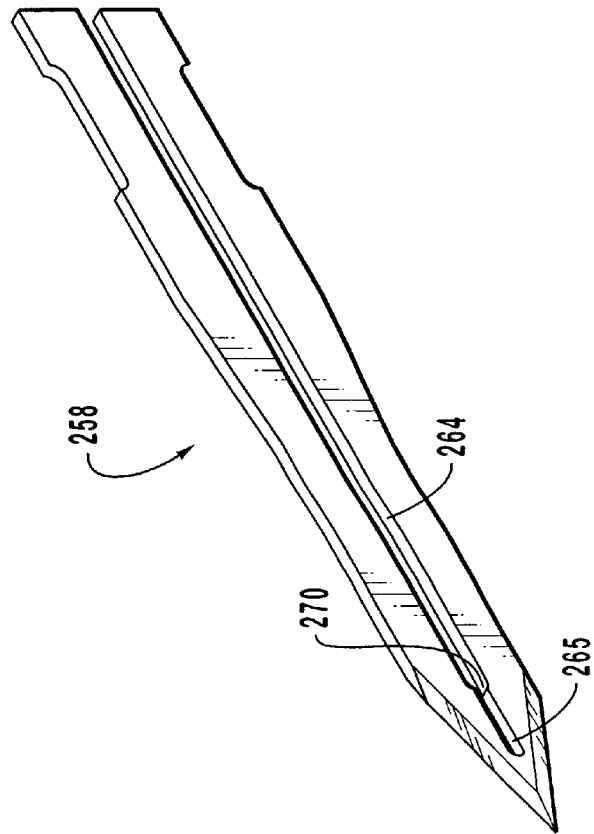
Figure 13:
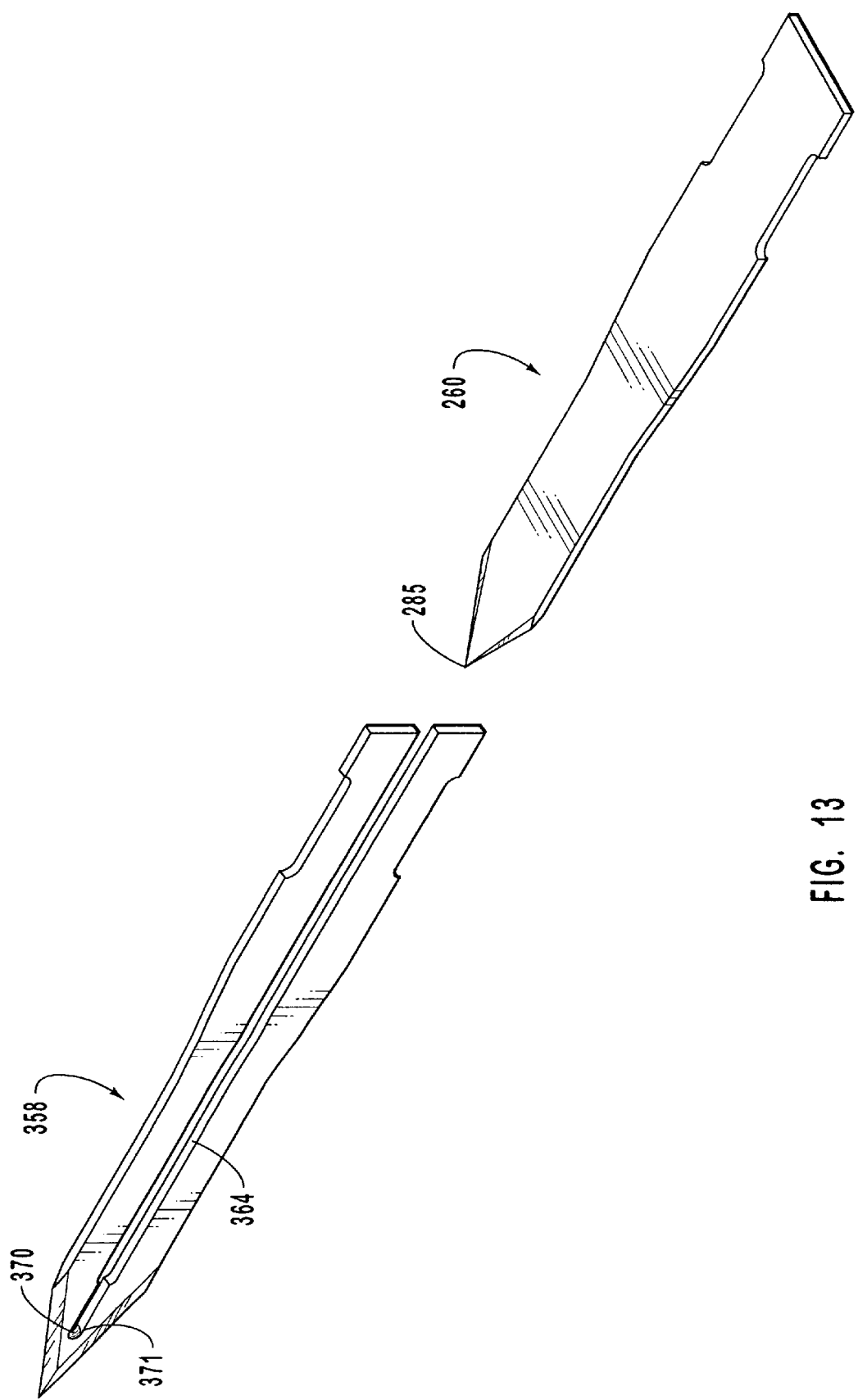
FIG. 13 is an exploded perspective view of another configuration of the alternate embodiment of FIG. 10.
Figure 14:
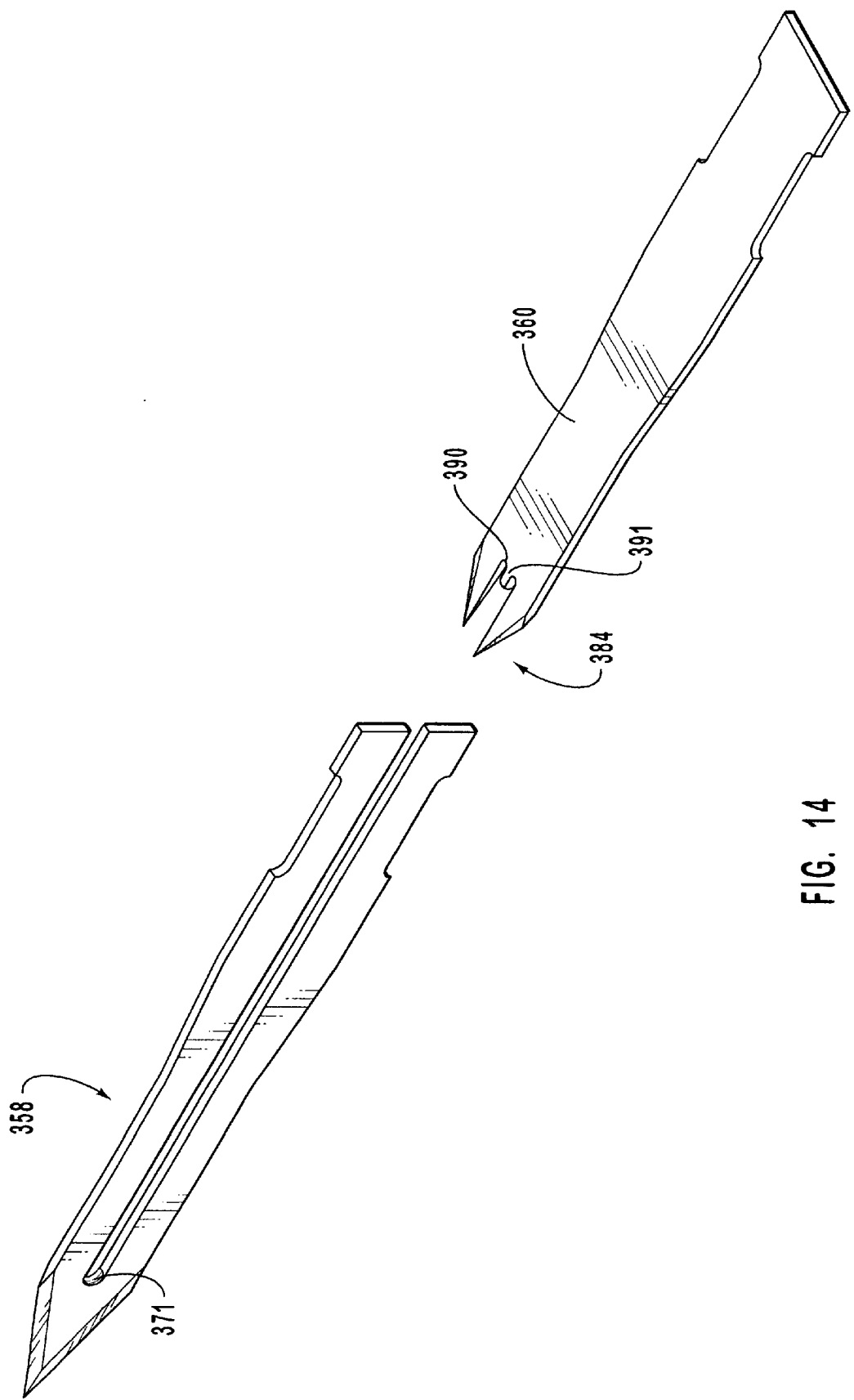
FIG. 14 is an exploded perspective view of another configuration of the alternate embodiment of FIG. 10.

In another configuration, as depicted in FIG. 12, primary blade 258 may be formed with a slot 265 which extends from a bifurcation point 270 towards sharpened distal point 276. Slot 265 has dimensions smaller than slot 264 and is configured to cooperate with a secondary blade 260 which has a sharpened distal point 285 similar to sharpened distal point 276 of primary blade 258. In another configuration, as shown in FIG. 13, primary blade 358 is formed with a recess 371 located at the distal end of slot 365 such that sharpened distal point 285 of secondary blade 260 may be located therein and fixably coupled thereto. In yet another configuration, as shown in FIG. 14, secondary blade 360 is formed with a protrusion 391 located at bifurcation point 390 and extending from bifurcation point 390 towards distal end 384. Protrusion 391 cooperates with recess 371 formed in primary blade 358 such that primary blade 358 and secondary blade 360 are fixably attached together.

It can be appreciated that various other configurations and methods of coupling primary and secondary blades may be accomplished, in addition to numerous configurations of the multi-bladed portion of the aortic knife. Such features as shapes, configurations, number of the blades or the manner of their connection to each other may vary without departing from the spirit of the present invention as long as some of the blades have their distal ends off-set or spaced longitudinally in a proximal direction from the distal sharpened point of another blades. For example, a multi-bladed portion may contain a plurality of blades, including two blades. The number of primary blades may be the same or different from the number of the secondary blades, it also may be odd or even. Similarly, the multi-bladed portion of the knife, containing primary and secondary blades, may be formed as a unitary piece, for example, by stamping or welding. In this case, there will be no need in forming slots, such as 164 or 265 shown in FIGS. 11–14 for connection of the blades to each other. As another example, primary and secondary blades may be coupled by gluing, snapping, threading, push-and-twist connection, or in any other conventional manner without departing from a spirit of the present invention.

Through the various preferred configurations of the multi-bladed portion of the present invention as shown in FIG. 10, the sharpened distal points and sharpened edges of the primary blades come into contact with the aorta prior to the sharpened edges of the secondary blades. By so doing, less force is required to insert surgical knife 150 into a biological tissue, for example, the aorta thereby reducing the possibility of damage resulting to the back wall of the aorta during knife insertion. This new inventive configuration of the knife, as shown by way of example in FIG. 10, additionally provides a surgeon with increased control of the knife, compared with prior surgical knives, while giving smoother and more precise incisions.

The surgical knives described herein, may be formed from various types of material. For example, the multi-bladed portions may be formed from materials which are capable of retaining a cutting surface while meeting the requisite standards for surgical instruments. One example of material which is capable of fulfilling the requisite characteristics is surgical grade stainless steel.

In general, various sizes of the surgical knives described in reference to the present invention are available. It is preferred, for example, that aortic knives in accordance with the present invention are sized with respect to the various diameters of aortic punches available. Essentially, the aortic knife will be sized such that each knife diameter corresponds to an aortic punch size so that a surgeon can customize a desired fit. This offers uniform and precise incisions, and eliminates the lateral nicks associated with the conventional technique.

It is preferred that the aortic knife be slightly smaller in diameter than the corresponding punch with which it is to be used. Once the anvil of the punch is inside the aorta, the shaft of the punch is centered and the punch is fired. It has been found that aortotomy punch sites created in this manner are much more uniform than those created with the conventional methods.

The present invention also relates to a method for using the aortic knife to facilitate a precise and improved incision. When a site or location and a size of the incision is determined, an appropriate surgical knife of the present invention is selected and inserted perpendicularly into the predetermined site to effectuate a multi-sided incision. In one exemplary application, the present invention relates to a method for using the aortic knife to facilitate creation of an aortotomy. A graft of a suitable diameter for use with a by-pass graft is dissected, brought to the aorta, and cut to an appropriate length. Antegrade cardioplegia is preferably supplied such that the aorta is filled and pressurized; the aorta is preferably full at the time of use of the aortic knife. A proximal anastomotic site is selected and the surrounding tissue is removed. An aortic punch is selected according to the diameter desired for the anastomosis. An aortic knife is then selected to advantageously correspond to the diameter of the aortic punch. A four-sided aortic knife is preferably passed perpendicularly into the aorta creating a cruciate, or "+" shaped, incision in the aorta An anvil of an aortic punch is then placed through the cruciate incision. The punch is centered and fired. Care is taken to avoid the back or opposite wall of the aorta An aortic knife in accordance with the present invention may alternatively be used to facilitate placement of an aortic cannula or other cannulae, or other medical instruments. In the preferred embodiment of the present invention, the incision opens in four directions as opposed to the linear incision associated with conventional scalpel techniques. Cannulation sites using the aortic knife and method associated therewith experience fewer problems with de-cannulation than those using conventional techniques. In addition, the method and apparatus of the present invention frequently provide a decrease in bleeding around the cannula at a cannulation site.

While certain parts of the present description of the invention specifically refer to "aortic knife", or use "for improving aortotomy," such reference is exemplary and the described knife or apparatus for effectuating improved incisions is not limited to use on aorta. The apparatus and method of the present invention may be used in other applications to create a body entry on any other biological tissue. For example, it may be any appropriate vessel, such as femoral artery. Alternatively, it may be other body organs, such as stomach or bowel.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for effectuating improved incisions, comprising:
   a multi-bladed portion for effectuating an incision, said multi-bladed portion comprising:
      a primary blade formed with a sharpened distal point; and
      a secondary blade coupled to said primary blade such that a distal end of said secondary blade is at a location proximally spaced from said sharpened distal point of said primary blade such that the distal points of the primary and secondary blades are staggered relative to each other; and
   a handle for manipulation of said multi-bladed portion, said handle comprising a distal end and a proximal end, said distal end of said handle being connected to said multi-bladed portion.

2. An apparatus as recited in claim 1, wherein said primary and said secondary blades are formed as a single piece.

3. An apparatus as recited in claim 1, wherein said primary and said secondary blades are snap-fitted to each other.

4. An apparatus as recited in claim 1, wherein said primary and said secondary blades are coupled by welding.

5. An apparatus as recited in claim 1, wherein said primary blade is formed with a longitudinal slot extending from a proximal end thereof to terminate at a point in close proximity to said sharpened distal point, said slot being formed to cooperate with said secondary blade.

6. An apparatus as recited in claim 1, wherein said secondary blade is formed with a longitudinal slot extending from a distal end thereof to terminate at a bifurcation point at a location proximal from said distal end.

7. An apparatus as recited in claim 1, wherein said primary blade is formed with at least two apexes.

8. An apparatus as recited in claim 1, wherein said secondary blade is formed with at least two apexes.

9. An apparatus as recited in claim 1, wherein said surgical knife is formed such that said at least two apexes formed on said primary blade and said at least two apexes formed on said secondary blade lie upon the same plane.

10. An apparatus as recited in claim 1, wherein said primary blade comprises at least two primary blade portions.

11. An apparatus as recited in claim 1, wherein said secondary blade comprises at least two secondary blade portions.

12. An apparatus as recited in claim 11, wherein the number of the primary blade portions equals the number of the secondary blade portions.

13. A method for effectuating improved incisions comprising the steps of:

selecting a site and a size for an incision;

obtaining a surgical knife suitable for use with the selected site and size, said surgical knife having a primary blade formed with a sharpened distal point and a secondary blade coupled to said primary blade such that a distal end of said secondary blade is at a location proximally spaced from said sharpened distal point such that the distal points of the primary and secondary blades are staggered relative to each other; and, inserting the surgical knife perpendicularly into the predetermined site, thus effectuating a multi-sided incision.

* * * * *